United States Patent
Glozman et al.

(10) Patent No.: US 8,348,861 B2
(45) Date of Patent: Jan. 8, 2013

(54) CONTROLLED STEERING OF A FLEXIBLE NEEDLE

(75) Inventors: Daniel Glozman, Kefar Adummim (IL); Moshe Shoham, Hamovil (IL)

(73) Assignee: Technion Research & Development Foundation Ltd., Haifa (IL)

(*) Notice: Subject to any disclaimer, the term of this patent is extended or adjusted under 35 U.S.C. 154(b) by 856 days.

(21) Appl. No.: 12/303,456

(22) PCT Filed: Jun. 5, 2007

(86) PCT No.: PCT/IL2007/000682
§ 371 (c)(1),
(2), (4) Date: Jan. 6, 2009

(87) PCT Pub. No.: WO2007/141784
PCT Pub. Date: Dec. 13, 2007

(65) Prior Publication Data
US 2009/0149867 A1  Jun. 11, 2009

Related U.S. Application Data

(60) Provisional application No. 60/810,705, filed on Jun. 5, 2006.

(51) Int. Cl.
*A61B 5/103* (2006.01)
(52) U.S. Cl. ......... 600/587; 600/585; 600/407; 606/130
(58) Field of Classification Search .......... 600/407–424, 600/508, 517, 518, 562, 585, 587; 606/130
See application file for complete search history.

(56) References Cited

U.S. PATENT DOCUMENTS

| | | | |
|---|---|---|---|
| 6,558,309 B2* | 5/2003 | Hogendijk et al. | 600/7 |
| 6,676,706 B1 | 1/2004 | Mears et al. | |
| 6,704,694 B1* | 3/2004 | Basdogan et al. | 703/4 |
| 7,102,635 B2* | 9/2006 | Shih et al. | 345/419 |
| 7,225,404 B1* | 5/2007 | Zilles et al. | 715/701 |
| 7,259,761 B2* | 8/2007 | Shih et al. | 345/419 |
| 7,850,456 B2* | 12/2010 | Chosack et al. | 434/272 |
| 2005/0203413 A1* | 9/2005 | Fichtinger et al. | 600/461 |
| 2007/0016067 A1* | 1/2007 | Webster et al. | 600/464 |
| 2007/0021738 A1* | 1/2007 | Hasser et al. | 606/1 |

(Continued)

OTHER PUBLICATIONS

International Search Report and Written Opinion in PCT/IL2007/000682, issued on Jul. 3, 2008.

(Continued)

*Primary Examiner* — Sanjay Cattungal
(74) *Attorney, Agent, or Firm* — Fish & Richardson P.C.

(57) ABSTRACT

A robotic system for steering a flexible needle during insertion into soft-tissue using imaging to determine the needle position. The control system calculates a needle tip trajectory that hits the desired target while avoiding potentially dangerous obstacles en route. Using an inverse kinematics algorithm, the maneuvers required of the needle base to cause the tip to follow this trajectory are calculated, such that the robot can perform controlled needle insertion. The insertion of a flexible needle into a deformable tissue is modeled as a linear beam supported by virtual springs, where the stiffness coefficients of the springs varies along the needle. The forward and inverse kinematics of the needle are solved analytically, enabling both path planning and correction in real-time. The needle shape is detected by image processing performed on fluoroscopic images. The stiffness properties of the tissue are calculated from the measured shape of the needle.

20 Claims, 8 Drawing Sheets

U.S. PATENT DOCUMENTS

| | | | | |
|---|---|---|---|---|
| 2008/0007517 | A9* | 1/2008 | Peshkin et al. | 345/156 |
| 2008/0010705 | A1* | 1/2008 | Quaid et al. | 901/8 |
| 2009/0036902 | A1* | 2/2009 | DiMaio et al. | 606/130 |
| 2010/0312129 | A1* | 12/2010 | Schecter | 600/508 |

OTHER PUBLICATIONS

D. Glozman et al, "Flexible Needle Steering and Optimal Trajectory Planning for Percutaneous Therapies", Proceedings of Medical Image Computing and Computer-Assisted Intervention—MICCAI 2004, Sep. 26-29, 2004, St Malo, France, Edited by C. Barillot et al, pp. 137-144, Springer, Berlin 2004.

D. Glozman et al, "Flexible Needle Steering for Percutaneous Therapies", ISRACAS-2004, 7th. Israeli Symposium on Compute-Aided Surgery, Medical Robotics, and Medical imaging, May 13, 2004, Petach Tikvah, Israel.

S.P. DiMaio et al, "Needle Steering and Model-Based Trajectory Planning", Proceedings of Medical Image Computing and Computer Assisted Intervention—MICCAI 2003, Nov. 15-18, 2003, Montreal, Edited by R.E. Ellis et al, pp. 33-40, Springer, Berlin, 2003.

M.D. O'Leary et al, "Robotic Needle Insertion: Effects of Friction and Needle Geometry", IEEE International Conference on Robotics and Automation, Taipei, Taiwan, Sep. 14-19, 2003, pp. 1774-1780.

* cited by examiner

US 8,348,861 B2

CONTROLLED STEERING OF A FLEXIBLE NEEDLE

CROSS REFERENCE TO PRIOR APPLICATIONS

This is a U.S. National Phase application under 35 U.S.C. §371 of International Patent Application No. PCT/IL2007/000682, filed Jun. 5, 2007, and claims the benefit of U.S. Provisional Application No. 60/810,705, filed Jun. 5, 2006 both of which are incorporated by reference herein. The International Application published in English on Dec. 13, 2007 as WO 2007/141784 under PCT Article 21(2).

FIELD OF THE INVENTION

The present invention relates to the field of percutaneous insertion of needles for therapeutic or diagnostic purposes, and especially to methods of guiding such needles to their target while avoiding sensitive organs en route.

BACKGROUND OF THE INVENTION

The trend of contemporary medicine is towards less invasive and more localized therapy. Many routine treatments employed in modern clinical practice involve percutaneous insertion of needles and catheters for biopsy and drug delivery. The aim of a needle insertion procedure is to place the tip of an appropriate needle safely and accurately in a lesion, organ or vessel. Examples of treatments requiring needle insertions include vaccinations, blood/fluid sampling, regional anesthesia, tissue biopsy, catheter insertion, cryogenic ablation, electrolytic ablation, brachytherapy, neurosurgery, deep brain stimulation and various minimally invasive surgeries.

In general, complications of percutaneous needle insertion are due to poor technique and needle placement. Physicians and surgeons often rely only upon kinesthetic feedback from the tool that they correlate with their own mental 3-D perception of anatomic structures. However, this method has significant limitations since as the needle penetrates the tissue, the tissue deforms and thus, even when working with straight rigid needles the needle might miss the target. To improve needle placement, rigid needles can be maneuvered under image guidance. In some cases the problem remains that rigid needles lead to excessive, injurious pressure on tissues. In a number of prior art documents, such as in US Patent Application No. 2007/0016067 to R. J. Webster III et al, there are described the use of beveled tip needles which are displaced during progression through a tissue because of the lateral deflection force imparted on the bevel tip by the tissue as the needle is pushed therethrough. Steering is accomplished by rotating the needle such that the bevel is oriented to generate the desired lateral deflection.

An alternative approach to ensuring the success of percutaneous procedures is to employ thin and flexible needles. There are numerous advantages to using such needles. Less serious complications occur with fine (less than 1 mm) biopsy needles than with standard coarse needles. Furthermore, thinner needles cause less damage and, for instance, have been shown to reduce the likelihood of Post Dural Puncture Headache (PDPH) after spinal anesthesia; indeed, the relative risk of PDPH decreases with reduction of needle diameter. Moreover, flexible needles facilitate curved trajectories that can be desirable in order to avoid sensitive tissues, such as bone or blood vessels or sensitive nerves or organs which might lie between feasible entry points and potential targets. However, a major disadvantage to using thin flexible needles is that they are difficult to control. They have non-minimum phase behavior and do not lend themselves to intuitive (human) control.

Devising a method to predict flexible needle motion was first addressed by DiMaio et al. in the article entitled "Needle Steering and Model-Based Trajectory Planning", published in *Proceedings of Medical Image Computing and Computer-Assisted Intervention*, Montreal, 2003, pp. 33-40, Springer. A limitation of this work is that due to the computation complexity, it does not allow for real-time simulation and control of the needle insertion.

In an article entitled "Flexible Needle Steering and optimal Trajectory Planning for Percutaneous Therapies", published in *Proceedings of Medical Image Computing and Computer-Assisted Intervention*, Saint-Malo 2004, pp. 137-144 Springer, it was demonstrated by the inventors in the present application that the needle tip path is not unique and can be optimized to minimize lateral pressure of the needle body on the tissue.

The disclosures of each of the publications mentioned in this section and in other sections of the specification, are hereby incorporated by reference, each in its entirety.

SUMMARY OF THE INVENTION

The present invention seeks to provide a new, computer controlled robotic system, and associated method, for closed-loop steering of a flexible needle during insertion into soft-tissue, using imaging to determine the needle position. The control system calculates a needle tip trajectory that hits the desired target while avoiding en route obstacles, impingement on which may be potentially dangerous to the subject. The system then preferably utilizes an inverse kinematics algorithm, to calculate the maneuvers required of the needle base to cause the tip to follow the desired trajectory, such that the robot can perform controlled needle insertion.

According to one preferred embodiment, the insertion of the flexible needle into a deformable tissue is modeled as a linear beam supported by virtual springs, where the stiffness coefficients of the springs varies along the needle. The forward and inverse kinematics of the needle are solved analytically, using a low dimensional linear system of equations, enabling both fast path planning and correction in real-time. The model enables path planning and its optimization for minimal tissue pressure. The model can be solved in a closed-form for a given needle tip trajectory. The needle path shape is preferably detected by image processing performed on fluoroscopic images, though other detection methods may also be used.

According to another preferred embodiment of the present invention, the controller also uses the shape of the needle as detected from the images, to continuously determine the properties of the tissue through which the needle is passing at any moment, and these tissue properties are then used as an additional input to the control system to correctly adjust the needle path according to the tissue being negotiated.

The planning, calculation and monitoring of the needle trajectory is preferably performed in a two dimensional plane, which includes the direction of the insertion process, and a direction generally perpendicular to the imaging direction of the fluoroscope system. This arises from the general convenience of the method of viewing the process direction of the insertion process on a two dimensional fluoroscope image, preferably on a C-arm system. In such a case, the robot base is required to impart motion to the needle base in at least the insertion direction and the direction in the imaging plane perpendicular thereto, and in addition, angular motion at least in a plane parallel to the imaging plane. In this simple case, when only a two dimensional path is used, a method should preferably be provided for determining if the needle tip deviates from the desired plane, so that correction movements can also be supplied by the robot to return it to the preplanned plane. According to one preferred embodiment, this deviation can be determined by use of a force sensor aligned to detect forces perpendicular to the imaging plane.

However, it is to be understood that, if a more complex three dimensional imaging or position determining system is used for implementing the invention, a trajectory in three dimensions can be planned, calculated and monitored.

According to further preferred embodiments of the present invention, miniature position transmission sensors may be attached at various positions along the length of the needle to monitor the needle's progress during insertion, thus significantly reducing the number of X-ray images required during insertion. According to these embodiments, it may well be sufficient to take only one image at the beginning of the process to determine the target and obstacle positions, and one at the end to ascertain correct positioning of the tip before the desired therapeutic or diagnostic action is performed.

There is thus provided in accordance with a preferred embodiment of the present invention, a a system for the insertion of a needle having a tip into a tissue, according to a predetermined trajectory, comprising:

a robot for maneuvering the needle into the tissue, an imaging system for ascertaining the trajectory of the needle in real time, and a control system controlling the robot motion according to differences between the ascertained trajectory and the predetermined trajectory, wherein the controller utilizes a model of the needle as a flexible beam having a plurality of virtual springs connected laterally thereto to simulate lateral forces exerted by the tissue on the needle, and whose trajectory through the tissue is determined by the influence of the plurality of virtual springs on the needle.

In accordance with another preferred embodiment of the present invention, the system determines the needle trajectory taking into account the effect of motion of the tissue as a result of insertion of the needle. Additionally, the system may preferably determine the needle trajectory taking into account the change in the stiffness coefficients of at least some of the virtual springs as a result of the trajectory of the needle.

In any of the above-described systems, the predetermined trajectory of the needle preferably comprises a target for the tip of the needle, and it may further comprise at least one region where access is forbidden to the needle.

There is further provided in accordance with still another preferred embodiment of the present invention, a system as described above, wherein the robot motion comprises at least some of inward, lateral and angular motion. The robot motion may preferably comprise up to 6 degrees of freedom.

In accordance with a further preferred embodiment of the present invention, in any of the above described systems, the imaging system may be any one of an X-ray fluoroscopic system, a CT system, an MRI system, an ultrasonic system, a system using electromagnetic navigation, and a system using optical navigation. Furthermore, the imaging system is preferably aligned to provide images of a plane generally including the directions of the lateral and inward motion.

There is also provided in accordance with a further preferred embodiment of the present invention, a system as described above, wherein the control system determines the deviation of the real time position of the tip determined by image processing of an image obtained from the imaging system, from the planned position of the tip according to the predetermined trajectory, and calculates the motion to be applied to the robot to reduce the deviation by use of the virtual springs model.

The control system may preferably utilize an inverse kinematics solution applied to the virtual springs model to calculate the required motion to be imparted to the needle to follow the planned trajectory. Additionally, the control system may also use the shape of the needle as detected from the images, to determine in real time changes in the stiffness properties of the tissue which the needle is traversing. In such a case, the control system may preferably use these changed tissue properties to adjust the needle path in real time in accordance with the tissue being negotiated.

Additionally and preferably, the system may comprise a force sensor to determine the forces exerted on the needle at its base, and the control system may then also use these forces to determine in real time changes in the stiffness properties of the tissue which the needle is traversing.

In accordance with a further preferred embodiment of the present invention, there is also provided a system as described above, and in which the predetermined trajectory is divided into increments, and the control system performs the insertion according to these increments, and in accordance with the real time results obtained at least from the imaging system at each incremental insertion point.

Furthermore, in accordance with yet another preferred embodiment of the present invention, the needle may comprise at least one position sensor, such that the needle can be detected using the at least one position sensor. The at least one position sensor may preferably be an electromagnetic position sensor. In either of these cases, the system preferably further comprises a registration system such that the co-ordinate system of the robot, to which the needle is attached, can be related to the co-ordinate system of the imaging system in which the tissue features are determined.

There is further provided in accordance with yet another preferred embodiment of the present invention, a system for controlling the insertion of a needle into a deformable tissue, according to a predetermined trajectory, comprising:

a robot for maneuvering the needle into the tissue, an imaging system for ascertaining the trajectory of the needle in real time, and a control system controlling the robot motion according to differences between the ascertained trajectory and the predetermined trajectory, wherein the control system:

(i) uses the trajectory of the imaged needle to determine changes in the elastic properties of the tissue through which the needle is passing, ii) utilizes these tissue properties to adjust, according to the tissue being negotiated, an elastic model of the tissue along the path of the needle, (iii) obtains an inverse kinematic solution for the motion of the needle though the tissue, and (iv) instructs the robot to maneuver the needle into the tissue according to the solution.

Such a system preferably may also comprise a force sensor to determine the forces exerted on the needle at its base, and the control system preferably then performs the additional step of also using the forces to determine changes in the elastic properties of the tissue which the needle is traversing. In such a system, the predetermined trajectory may preferably be divided into increments, and the control system can then perform the insertion incrementally according to the real time results obtained from the imaging system.

In accordance with still another preferred embodiment of the present invention, there is also provided a method of controlling the insertion of a needle into a tissue, comprising the steps of:

determining a preplanned trajectory to be followed by the needle, mounting the base of the needle on a robot for maneuvering the needle into the tissue, generating images of the tissue to show the trajectory of the needle in real time, controlling the motion of the robot according to differences between the real-time trajectory and the preplanned trajectory, and utilizing a model of the needle as a flexible beam having a plurality of virtual springs connected laterally thereto to simulate lateral forces exerted by the tissue on the needle, and calculating the trajectory through the tissue on the basis of the influence of the plurality of virtual springs on the needle.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1:
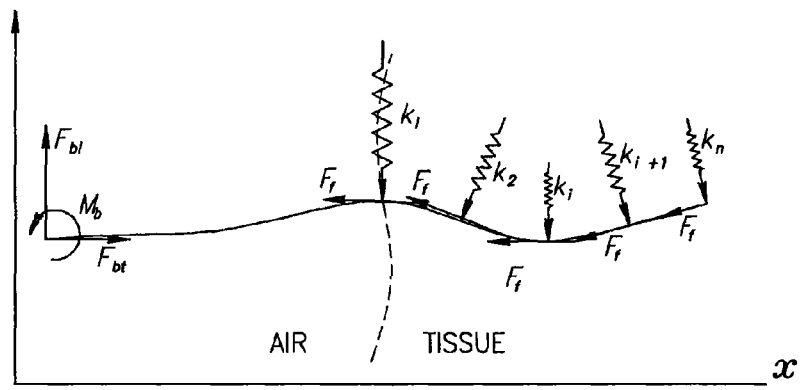
FIG. 1 illustrates schematically a prior art model of the interaction of the tissue with the needle as represented by a series of distributed virtual springs.

Reference is now made to FIG. 1, which illustrates schematically a model of the interaction of the tissue with the needle as represented by a series of distributed virtual springs, having coefficients $k_1, k_2, \ldots k_n$ as first used in the abovementioned MICCAI 2003 article by the present inventors. The tissue surface is denoted in FIG. 1 by the dashed line. The modeling of flexible needle movements is based on the assumption of quasistatic motion; the needle is in an equilibrium state at each step. It is known that needle deflection due to interactions with biologic soft tissue is nonlinear with strain. However, it is reasonable to assume a linear lateral force response for small displacements. Thus, the tissue forces on the needle are modeled as a combination of lateral virtual springs distributed along the needle curve plus friction forces $F_f$ tangential to the needle. Since the tissue elastic modulus changes as a function of strain, the coefficients, k, of the virtual springs are updated according to the strain-dependent dynamic elastic modulus and the system is linearized at each step.

As the shape of the needle changes, the location and orientation of the virtual springs change accordingly. The linearized system model yields the shape of the needle at each step. There is no physical meaning for the free length of the virtual springs. The only important parameter of a spring is the local stiffness coefficient that expresses the force of the tissue on the needle as a function of local displacement. The stiffness coefficients of the virtual springs are determined experimentally or by using preoperative images assuming empiric stiffness values of tissues and organs.

Figure 2:
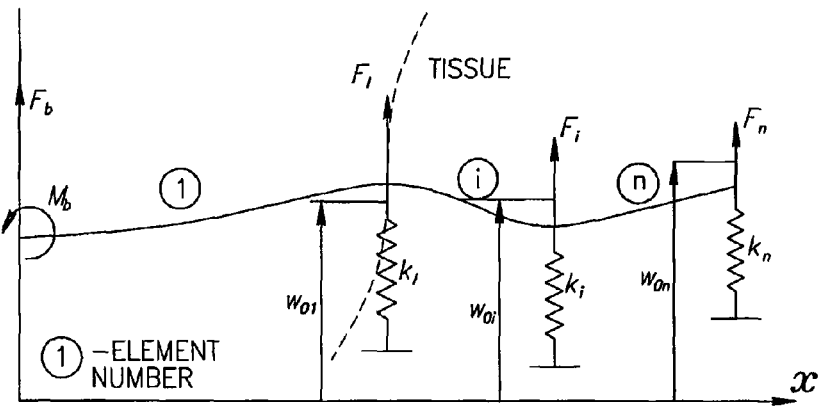
FIG. 2 schematically illustrates the needle as approximated by a linear beam subjected to point forces, assuming small displacements.

Reference is now made to FIG. 2 which schematically illustrates the needle as approximated by a linear beam subjected to point forces, assuming small displacements. This enables the calculation to be performed to a first approximation, as if all of the virtual springs are connected to the beam at right angles, thus simplifying the calculation. However, it should be noted that even if the linear approximation solution is not strictly accurate, one outcome of the use of a closed loop control system to apply its results to the problem of a needle insertion is that any inaccuracies in the calculation assumptions are corrected by the ultimate iterative nature of the application. With appropriate spacing of elements, the beam can approximate a flexible beam according to the elastic foundation model.

At each joint, the force applied by a virtual spring is proportional to the displacement of the spring from its initial position:

$$F_i = k_i(w_i - w_{0i}) \tag{1}$$

where $k_i$ is the virtual spring coefficient, $w_i$ is the displacement at point i, and $w_{0i}$ is the position of freed spring i.

Since the forces are a function of the deflection, the needle movement cannot be modeled by treating the beam as one element. Therefore the beam is split into a number of elements, so that each beam element is subjected to two neighboring forces. The first element, marked 1, is that part of the needle outside of the tissue, and the rest of the elements, marked i, ... n, are distributed along the inner part of the needle within the tissue, according to the level of discretization. Each element behaves as a linear beam subjected to shearing forces at its borders. The displacement of each element is given by a third degree polynomial. Using the nodal degrees of freedom from finite elements theory, the coordinates are identified specifically with a single nodal point and represent a displacement or rotation, having clear physical interpretation. The displacement y(x) has the form:

$$y(x) = N_1 \phi_1 + N_2 \phi_2 + N_3 \phi_3 + N_4 \phi_4 \qquad (2)$$

where $N_1, N_3$ are the coordinates and $N_2, N_4$ are the slopes at x=0 and x=1 of an element, respectively. $\phi_i$ are the shape functions of third degree.

Substituting boundary conditions as displacement and slope at the base and tip of the needle result is 4×n equations, two at each side and four for each internal node, which yields the global matrix equation:

$$[K]\bar{N} = \bar{Q} \qquad (3)$$

where K is the matrix of coefficients of $N_{i,j}$-translation and slope degrees of freedom. N is the vector of $N_{i,j}$, where i is the element number and j is the degree of freedom of element i.

Given the translation and a rotation of the needle base, (3) is used to calculate the 3-DOF (Degrees Of Freedom) translation and rotation of the needle tip, which gives the forward kinematics solution.

In a real-life needle insertion problem, there is a need to hit the target with the tip while at the same time avoiding possible organ obstacles on the way as the tip is inserted. So a particular trajectory is desired for the tip of the needle and it is the manipulation done at the needle base that it is necessary to calculate to generate the desired trajectory. This is an inverse kinematics problem; namely, given the position and orientation of the tip trajectory, the translation and orientation of the needle base are derived as a function of needle progress into the tissue. One solution of the inverse kinematics problem can be obtained by manipulations and inversion of (3), as described in detail in the above mentioned article by S. P. DiMaio et al.

Planning a linear insertion path is a trivial task. The need to avoid obstacles while applying minimal lateral pressure on the tissue is a more complex problem. The optimal needle path is one where there is minimal curvature of the needle, since this imparts minimal lateral pressure on the tissue. The path planning problem thus reduces to finding preferably the shortest curve that connects the target to the needle insertion point, and which avoids the obstacle by a predetermined distance while maintaining minimal needle curvature.

Figure 3:
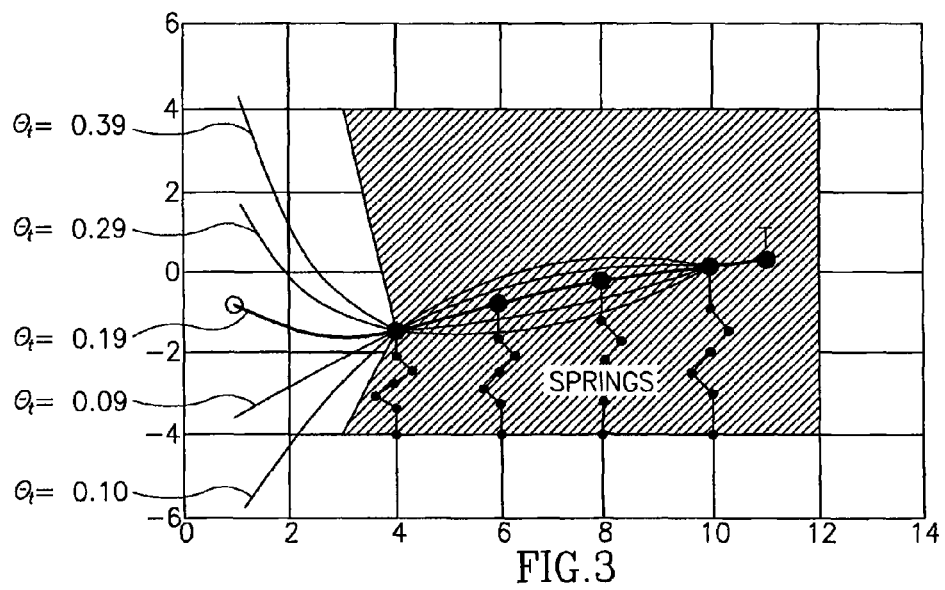
FIG. 3 shows several different needle path solutions, according to a preferred embodiment of the present invention, where the same target point is reached with different tip inclinations θ.

Since every step is dependent on the history of the insertion, full simulation of the needle insertion is required. Reference is now made to FIG. 3 which shows several different needle path solutions, where the same target point T is reached from the same insertion point, but with different tip inclinations θ to the horizontal, (assuming that the graph represents a side view of the subject's region of treatment) where θ is measured in radians. As is seen, different trajectories can be used to reach the same target point, each one circumventing a different potential obstacle region, and each one having its own lateral pressure profile on the subject's tissue. In FIG. 3, the abscissa is the beam element number, while the ordinate is the deflection distance from the vertical position of the target point.

Since in biopsy, the orientation of the tip is of less importance, the solution that applies minimal pressure on the tissue can be chosen from the infinite number of solutions. This is achieved by minimizing the sum of squares of the deflections of the virtual springs, the sum of which is given by S:

$$S = \min \sum_{i=1}^{n} (w_i^2 + \theta_i^2) = \min \sum_{i=1}^{n} \sum_{j=1}^{4} N_{ij}^2 \qquad (4)$$

Differentiating (4) with respect to $\theta_t$ and equating to zero, equation (5) is obtained:

$$\frac{dS}{d\theta_t} = \sum_{i=1}^{n} \sum_{j=1}^{4} 2N_{ij} \frac{dN_{ij}}{d\theta_t} = 0 \qquad (5)$$

Equation (5) is then substituted into (3) in place of equation of the slope of the last element $N_{4n}$ and the solution of (3) gives the optimized needle shape.

Figure 4:
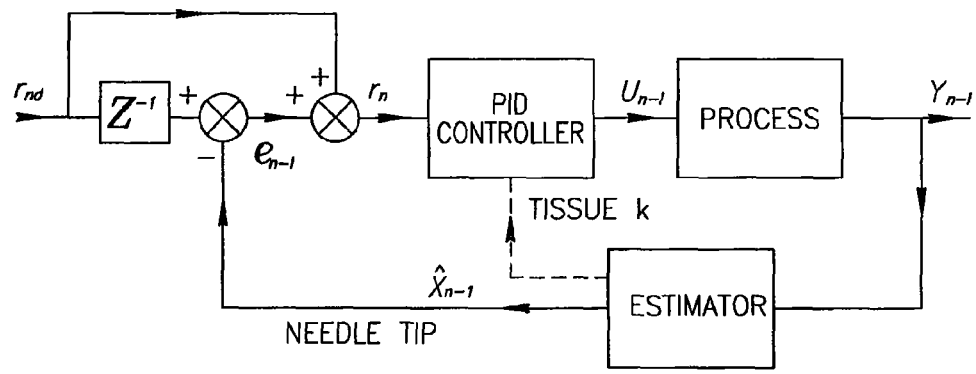
FIG. 4 shows a control algorithm for determining the needle trajectory, according to a further preferred embodiment of the present invention.

Reference is now made to FIG. 4, which shows a control algorithm for determining the needle trajectory, according to a further preferred embodiment of the present invention. The input to the system $r_{nd}$ is the desired location of the needle tip excluding its orientation, which is later optimized by a controller. The index nd is for the desired iteration step n. The controller input is the desired position of the needle tip $r_{nd}$, plus the tip position error $e_{n-1}$ from the previous iteration. The addition of the tip position error from the previous iteration is done in order to define a desired tip position beyond that achieved, in order to generate overcompensation in the next iteration to bring the tip position closer to the desired position. The controller runs an inverse kinematics solution of the flexible needle, as described hereinabove, plus optimization for minimal needle deflections, or minimum tissue distortion all as described in equations (4) and (5) above. The controller outputs are the required coordinates of the needle base $U_{n-1}$ that are calculated from the inverse kinematics calculations. These outputs are fed to the robot which moves the needle base accordingly, inwardly, laterally and angularly, to its next iterative position. The process itself includes the robot that moves the needle base, the mutual interaction of the tissue and the needle, the force sensor, and the needle shape detection algorithm. The needle shape algorithm preferably utilizes image processing performed on images of the needle, in order to determine the shape of the needle and the coordinates of the needle tip, $Y_{n-1}$. The estimator receives the needle shape and the force sensor measurement and calculates therefrom the tissue stiffness profile, in terms of updated $k_i$. The new tissue stiffness profile parameters $k_i$ are then used to update the inverse kinematics solution, and to use these solutions in the next iterative step in the controller. In addition, the measured tip coordinate position $X_{n-1}$ is output from the estimator and is used to calculate the error from the desired position, also for use in the next iterative step. The measured tip coordinates $X_{n-1}$ minus the desired tip coordinates $r_{nd}$ is the tracking error $e_{n-1}$ for that iteration, and is added to the desired tip position as the new input to the controller, whereupon the next iteration proceeds as described above. Although the controller is shown as a PID controller in FIG. 4, it is to be understood that the invention is not meant to be limited to this mode of control.

Figure 5A:
FIG. 5A is a representations of a fluoroscope image of a typical needle image after insertion.

Reference is now made to FIG. 5A, which is a representation of a fluoroscope image of a typical needle after insertion.

Figure 5B:
FIG. 5B is a preferred example of a filter for detecting the needle base shape and its location by normalized cross-correlation with the original image.

Detection by means of image processing begins from the needle base and follows the needle body from that point. The flexible (spinal) needle has a clearly detectable base shape and its location is detected by normalized cross-correlation of the original image, preferably with the filter shown in FIG. 5B. Cross-correlation is a very efficient tool for matching images. It is generally robust to noise, and can be normalized to allow pattern matching independently of scale and offset in the images. Cross-correlation with the whole image is preferably performed only once. Following the first detection, the filter is cross-correlated with only a small square around the previously detected coordinates to save execution time and to avoid false detections. Once the base of the needle is detected, the rest of the needle is tracked by following the low gradient area of the 3D representation of the image, as is known in the art of image processing.

Needle tip detection at the end of the low gradient is not straightforward. The surrounding soft tissue is not totally X-Ray radiolucent and the difference in grey shade between the tissue and the needle is small. Also any obstruction, like beads, can make needle tip detection even more difficult. Since the length of the needle is constant, it represents an additional parameter useful for determining the position of the needle tip. Therefore, in addition to grey shade differences, the length of the needle is accounted at each step.

Because of the noisiness of images, not all the detected points lie on the real needle projection, therefore the needle is fitted using a polynomial that smoothes the noisy data.

The control error is defined as the positional deviation of the tip from its planned trajectory. The error is calculated at each step and the next requested needle position is set into the planned curve direction with magnitude determined by the controller.

Since a vision system is preferably utilized in detecting the shape of the needle, it is possible to obtain the properties of the tissue from the response of the needle, namely from the needle shape. During needle insertion, the points where the virtual springs have penetrated and the position and orientation of the element nodes are tracked.

In the construction of (4) the concentrated force boundary condition between the elements was used and is defined by:

$$EI\frac{d^3 V}{dx^3} = k_n(N_{n,3} - Vk_n) + k_{n+1}(N_{n+1,3} - Vk_{n+1}) \quad (6)$$

where the expression $(N_{n,3} - W_{0,n})$ represents the deflection of the spring $N_{n,3}$ from its relaxed position $w_{0,n}$.
For the last tip element, this moment is given by:

$$EI\frac{d^3 V}{dx^3} = k_n(N_{n,3} - Vk_n) \quad (7)$$

since the last element length is shorter than any other and the moment applied on it is negligible.

$$\frac{d^3 V}{dx^3} = \frac{12N_{n,1}}{l_n^3} - \frac{6N_{n,2}}{l_n^2} - \frac{12N_{n,3}}{l_n^3} - \frac{6N_{n,4}}{l_n^2} \quad (8)$$

When the shape of the needle is known, the values of displacements and slopes at the nodes are calculated as well as the moments at the nodes from (8). Then starting from the last node the stiffness coefficients of the springs are calculated to obtain the initially detected shape of the needle from (6) and (7).

Figure 6:
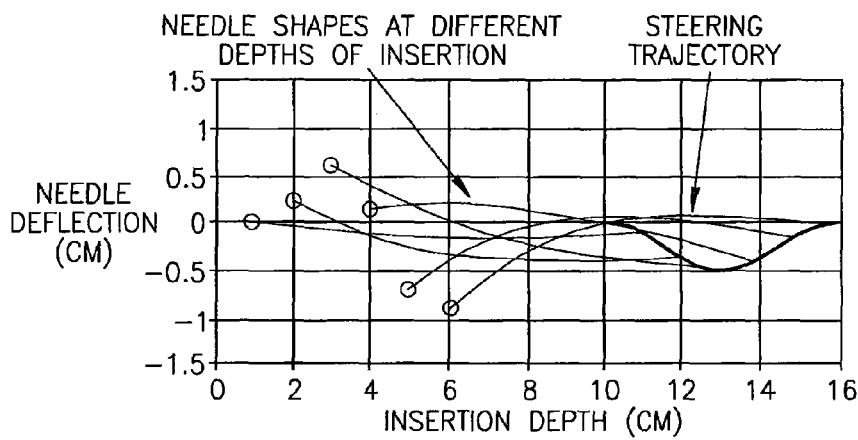
FIG. 6 shows the progress of a typical flexible needle insertion, causing the needle tip to follow a half sine wave.

Reference is now made to FIG. 6 which shows schematically a sequence of a typical flexible needle insertion, causing the needle tip to follow a half sine wave shape. Each line represents the needle flexed shape at different depths of insertion. The stiffness coefficients of the virtual springs for the example shown in FIG. 6 are taken as 10 N/mm.

Figure 7:
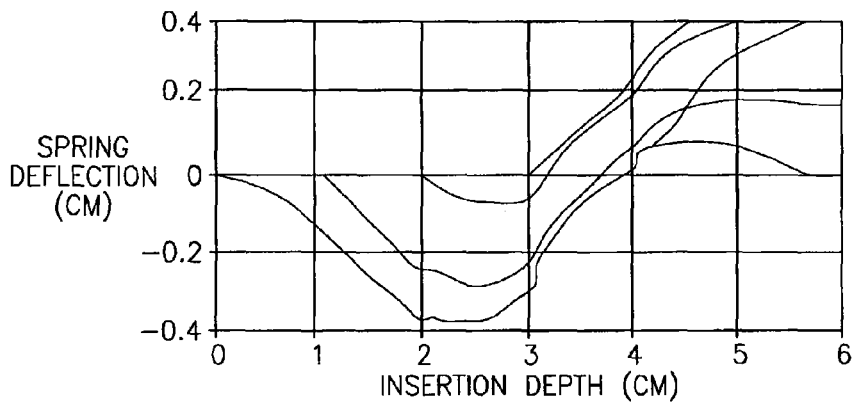
FIG. 7 is a graphic depiction of the deflections of six virtual springs along the trajectory, labeled as numbers 1 to 6 along the abscissa, each spring engaging only when the tip passes its location.

FIG. 7 is a graphic depiction of the deflections of six virtual springs along the trajectory, labeled as numbers 1 to 6 along the abscissa, each spring engaging only when the tip passes its location.

Figure 8:
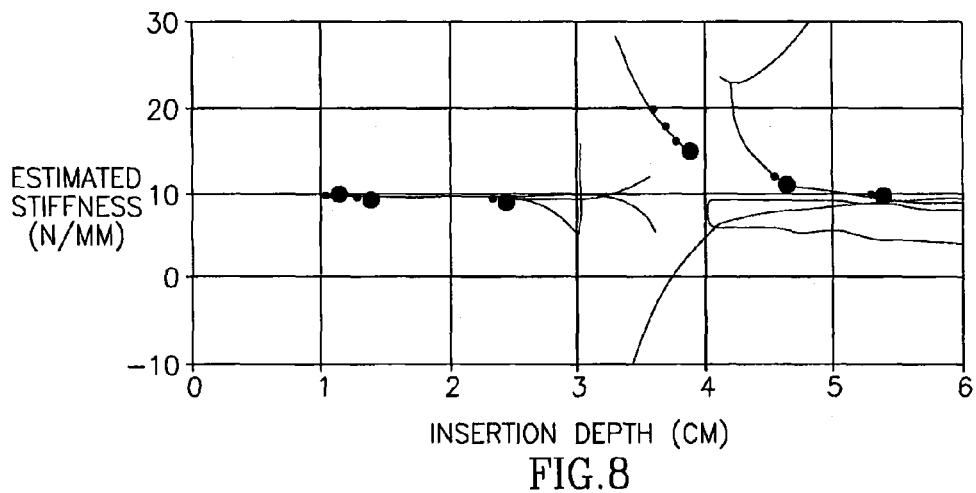
FIG. 8 shows the spline fitted needle shape, as a function of the tip insertion depth.

The estimated stiffness coefficients of the springs are calculated from the spline fitted needle shape, and are shown as a function of the tip depth in FIG. 8. When the displacement of a spring is very small it is impossible to accurately calculate the stiffness of the spring from (6), because of the division by a very small number. The graphs depicting calculated stiffness coefficients are shown only for values of deflection larger than 0.05 mm. It can be seen that the graphs converge at the simulated value of the spring coefficient, 10 N/mm. The stiffness coefficient value is considered reliable after three successive iterations, depicted by circles on the drawing.

An advantage of this method is the ability to estimate or correct for tissue stiffness at the time of the insertion without any prior knowledge of the tissue stiffness expected.

Figure 9A:
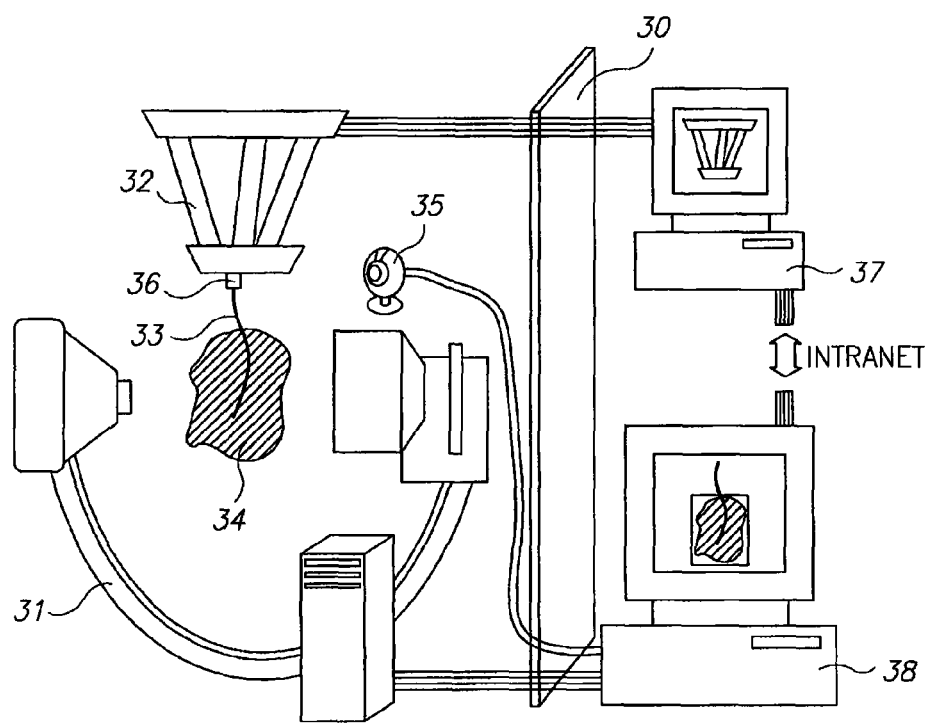
FIG. 9A is a schematic illustration of a system, constructed and operative according to a preferred embodiment of the present invention, for performing controlled needle insertion.

Reference is now made to FIG. 9A, which is a schematic illustration of a system, constructed and operative according to a preferred embodiment of the present invention, for performing controlled needle insertion. The treatment region is separated from the control region by an X-Ray opaque shield 30, preferably made of lead sheet. The imaging of the insertion progress in the subject's tissue is preferably performed using a C-arm fluoroscope system 31, this being a convenient and widely available system. However, any other suitable method of medical imaging is equally well acceptable for use in this invention, such as CT, ultrasound, MRI. The C-Arm 31 used in the experimental arrangement to test the feasibility of the system shown in this preferred embodiment was a Siemens Multimobil 5C with nominal intensifier diameter of 230 mm and highest image resolution of 756×562 pixels. The digital image is received from one of the C-Arm monitors by a DFG/1394-1e video-to-FireWire converter supplied by Imaging Source Europe GmbH. In order to oversee progress of the procedure, an optional Logitech USB digital camera 35 is preferably placed facing the insertion site, such that the robot 32, the needle 33 and tissue 34 can be viewed on the user screen.

A RSPR 6DOF parallel robot 32, is preferably used for holding the needle 33, and for aligning and propelling it into the patient's tissue 34. It is to be understood though, that the invention is not limited to a parallel robot structure, but that any serial, parallel or hybrid robotic structure may be used. The RSPR robot workspace can be approximated by a cylinder of 25 mm diameter and 50 mm height, which can be covered with plate angles of up to 20 degrees. The needle is preferably connected to the robot's moving plate by a 6-DOF force/torque transducer 36, which measures needle insertion forces and torques.

In the embodiment of the system illustrated in FIG. 9A a separate computer 37 preferably performs the calculations determining robot control algorithm and runs the robot control loop at 500 Hz. Its function is to obtain the desired needle base coordinates, preferably via a network or serial or other computer interface, and to control the robot so that it moves the needle base to the requested coordinates. The control loop is responsible for sampling the network for incoming packets from the main computer, which can be movement commands, position, or force requests.

The main computer is the needle control computer 38 that preferably is responsible for the image processing, needle and tissue detections as well as needle control. The main computer 38 commands the motions of the robot via the robot controlling computer 37. It is to be understood though that the control system may equally well be built around a single computing system.

Figure 9B:
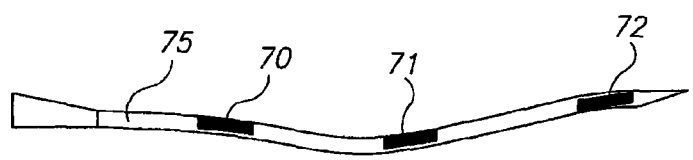
FIG. 9B is a schematic illustration of a needle using a number of miniature position sensors for use in another preferred embodiment of the system of FIG. 9A.

FIG. 9A has been described in terms of a C-arm system using an X-ray fluoroscope in order to determine the trajectory of the needle in real time as the needle is inserted. Reference is now made to FIG. 9B, which schematically illustrates an alternative method of determining the needle position using a number of miniature position sensors 70, 71, 72 mounted in the needle 75, for use in further preferred embodiments of the present invention. Such miniature position sensors, such as those obtained from Northern Digital Inc. (NDI) of Waterloo, Ontario, Canada, are generally based on the detection of induced voltages in tiny sensor coils in a controlled varying magnetic field. Such coils can be as small as about 0.5 mm in diameter×5 mm. long, making them suitable for mounting in a needle. In one such application, a single sensor coil is mounted in the tip of a flexible biopsy needle to monitor the tip position. According to NDI information, clinicians performing guided needle biopsies can then more accurately target the biopsy location, allowing navigation around critical structures, and decreasing the chance of false negative results. However, use in manual needle insertion may be of limited value for two reasons: (i) the location of the target may have moved with motion of the patient, or of the tissues themselves may have moved as a result of the needle insertion, and (ii) if the insertion is progressing incorrectly, no systematic means are available for diverting the tip towards the desired target.

According to further preferred embodiments of the present invention, the controlled needle insertion procedure is performed using such electro-magnetic position sensors mounted on the needle. Preferably, a number of sensors are mounted along the length of the needle, as shown in FIG. 9B, and the detected shape used instead of the fluoroscope for generating the needle position. Use of such sensors thus obviates steps 57 and 59 in the process flow chart shown in FIG. 10 below. Alternatively and preferably, a single sensor mounted in or close to the needle tip may be used. The available information regarding the needle's spatial situation can then be obtained from the position of the tip-sensor, its angular orientation in space, the position of the base of the needle as known from the robot position, and the force applied to the force sensor at each incremental step of the needle insertion. This information may be sufficient to define the needle path sufficiently for use with the controlled insertion technique of the present invention, to provide a method of controlled needle insertion without the use of potentially harmful accumulative X-radiation. Alternatively, it may be necessary to take one image at the outset, and one at the end of the procedure, in order to ensure proper placement of the tip. However, even in this case, the number of required X-ray images is greatly reduced.

The use of such position sensors in the needle may more readily enable the use of ultrasound imaging for the execution of the imaging processes of the present invention. It is known that flexible needles are not easily detected in ultrasound images, because of the way in which they reflect the ultrasound waves, such that mere replacement of the X-ray imaging with ultrasound imaging may be problematic without a method of enhancing the needle visibility. The position sensors of the present embodiment provide the needle with the visibility necessary to ensure the successful use of ultrasound imaging. However, in this case, since the needle position is determined on an imaging system (the position sensors) independent from that on which the tissue features (such as entry point, target point and obstacle regions) are imaged, it becomes necessary to perform a registration procedure such that the mutual orientation and position of the co-ordinate system of the robot, to which the needle is attached, should be known relative to the co-ordinate system of the ultrasonic imaging system in which the tissue features are known.

Several procedures must be completed in preparation for the insertion process. These procedures include, but are not limited to an X-Ray image distortion correction procedure, robot to image registration, tissue preparation, obstacles and target detection and initial measurements of qualitative tissue properties.

Images acquired using standard X-Ray equipment suffer typically from two independent geometric distortions: the geometry of the intensifier generates a pincushion distortion and the interaction of the Earth's magnetic field generates an imager-orientation dependent S-shaped distortion. Corrections for both of these distortions are known in the art. Images of a calibration grid fixed to the image intensifier are used for detection and subsequent compensation for these distortions; this is known as the dewarping procedure. The distortion is modeled by two bi-polynomials, which model independently the distorted $x_d$ and $y_d$ calibration bead coordinates as a function of the undistorted calibration bead coordinates $x_u$ and $y_u$:

$$x_d = \sum_{i=0}^{N} \sum_{j=0}^{M} P_{i,j}(x_u)^i(y_u)^j, \qquad (9)$$

$$y_d = \sum_{i=0}^{N} \sum_{j=0}^{M} Q_{i,j}(x_u)^i(y_u)^j$$

where $P_{i,j}$ and $Q_{i,j}$ are the coefficients of the degree N, M bi-polynomials. Using the matched distorted and undistorted bead positions, a system of linear equations is constructed and solved by QR factorization to recover the coefficients $P_{i,j}$ and $Q_{i,j}$.

Since the robot is mounted independently of the C-Arm, and each has its own coordinate system, there is a need to register one to the other in orientation and co-ordinate scale. In order to accomplish this, according to one preferred method, the robot is requested to reach three predefined points in its workspace. From these points the position, orientation and scale of the robot coordinate system relative to the C-arm image coordinate system is established.

The patient is aligned on the C-arm bed with the insertion region positioned close to the robot-held needle. The imaging plane must, of course, be perpendicular to the direction of needle insertion so that the insertion progress can be continuously monitored. The system operator is required to delineate the target and the obstacle on the X-Ray image obtained of the region of interest on the subject. If these two positions are not clearly definable in the image, such that image processing procedures can't identify them automatically, they should preferably be clearly marked in the image by using an image processing marker facility. Then, the markers or the positions themselves are detected in the delineated region in the same way as distortion correction calibration beads are detected. Since the target and the obstacle can move during needle insertion, their tracking is performed at every needle position sampling. A similar procedure is used for any other imaging method, such as CT.

According to one preferred method of executing the insertion procedure, a (316) stainless steel 22 gauge spinal needle is used, having an outer diameter of 0.711 mm and inside diameter of 0.394 mm, and which exhibits 193 GPa Young's modulus, and has a moment of inertia given by:

$$I = \frac{\pi}{64}(d_o^4 - d_i^4) = 11.361*10^{-3} mm^4 \quad (10)$$

Figure 10:
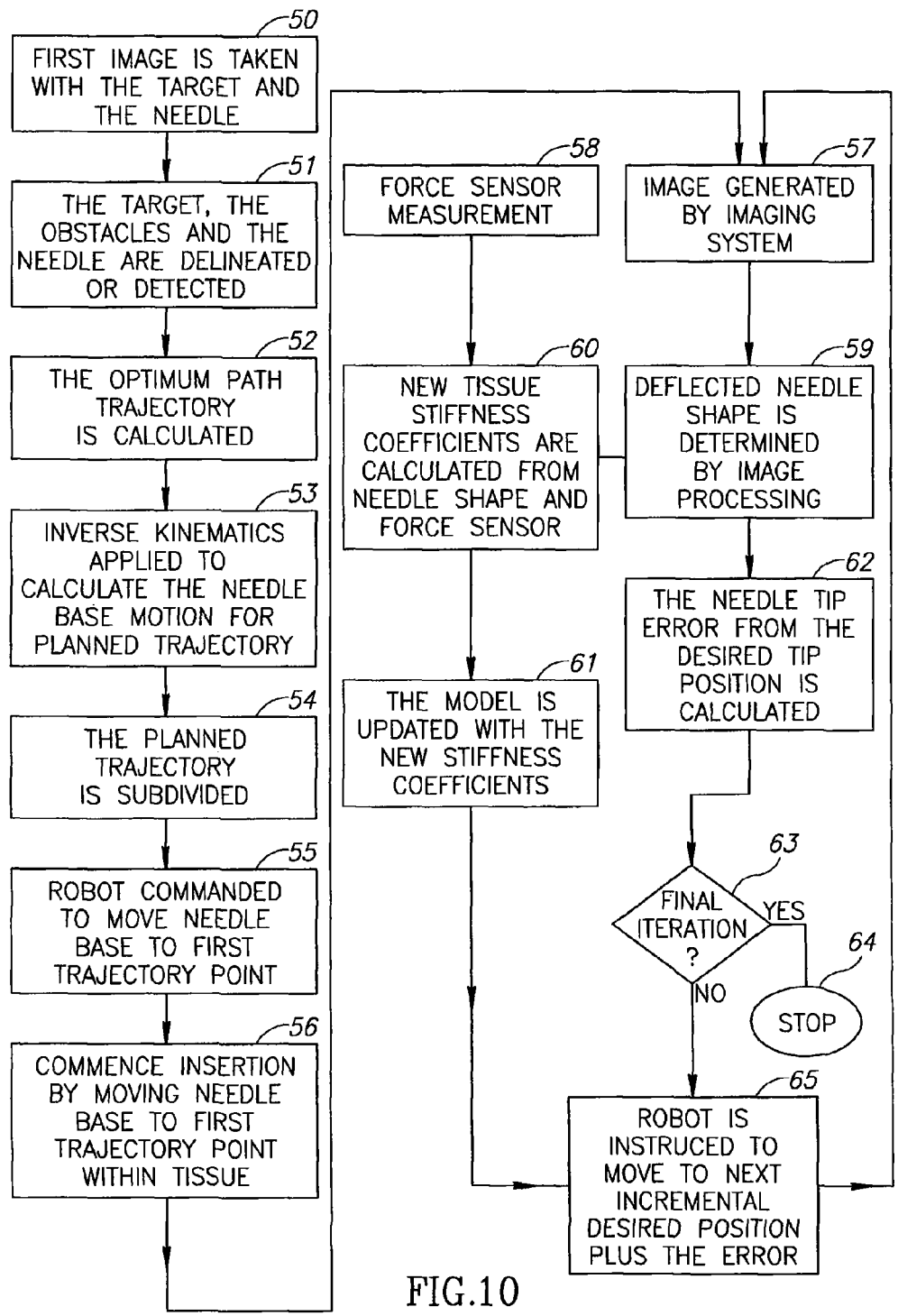
FIG. 10 is a flow chart, showing the steps in a method of insertion of a flexible needle, according to one preferred embodiment of the present invention.

Reference is now made to FIG. 10 which is a flow chart, showing the steps in a method of insertion of a flexible needle, according to one preferred embodiment of the present invention. The procedure is divided into two parts, steps 50 to 55, which are involved with the preparation for the controlled insertion, and the on-line control algorithm, in steps 56 to 65, which iteratively controls the insertion procedure itself.

In step 50, a first image is taken of the region of interest of the subject, at such an orientation as to show the target and the needle.

In step 51, the surgeon delineates with the help of a pointing device, such as a computer mouse, the target location and the areas that should be avoided. There is no need for him to delineate the needle itself, as that is automatically detected by the needle detection algorithm. The image is analyzed so that the target, any obstacle that needs to be avoided, and the needle are delineated or detected. This step therefore defines the constraints to the planned trajectory.

In step 52, the desired trajectory itself is defined, using the constraints determined in step 51. Usually, this desired trajectory will be the shortest path between insertion point and target point, while avoiding the obstacle by a predetermined distance.

In step 53, a calculation is made, using the inverse kinematics solution described above, to determine the series of needle base motions necessary in order that the tip of the needle follows the predetermined trajectory. The initially assumed values of the tissue stiffness coefficients are used in the first inverse kinematics calculation.

In step 54, the planned trajectory is divided into increments, according to the precision required, and the needle base motions are divided into corresponding increments.

In step 55, the robot is commanded to move to the first trajectory point, such that the needle tip just touches the surface of the tissue without any penetration, at the calculated position and angular alignment. This is the insertion point and represents the zero position of the iterative insertion procedure. It is at this position that a measurement is made of the initial tissue stiffness coefficients, as described below in association with FIG. 11.

In step 56, the robot receives a command from the control system to commence the insertion procedure itself, by moving the tip to the first trajectory point within the tissue. This robot movement results in needle insertion towards the next intended trajectory point, and tissue movement.

In step 57, after completion of the first movement increment, an image is taken of the site, using the X-ray fluoroscope, or a CT, or another imaging method, or an image synthesized from position sensors mounted on the needle itself.

In step 58, the force sensor mounted on the needle base determines the lateral force imposed by the tissue on the needle after this first incremental step.

In step 59, the position of the needle is determined, preferably by image processing from the X-ray fluoroscope image, or alternatively and preferably, from any of the other means described above. Since the needle insertion has also caused the tissue to move and its stiffness coefficients to change, the detected needle position is not generally that planned in the desired trajectory.

In step 60, the tissue stiffness parameters are recalculated using inputs from the force measurement performed in step 58 and from the resulting needle shape determined in step 59 from the image processing routine, or otherwise.

In step 61, the model of the trajectory using the initially assumed values of the tissue stiffness coefficients is updated using the newly determined coefficients from step 60.

At the same time, in step 62, the error in the position of the needle tip is calculated, for addition to the position reached in order to generate the desired position for the next incremental insertion step.

In step 63, the number of iterations is queried. If the planned number has been reached, the insertion is regarded as completed, and the process is stopped at step 64.

If the number of iterations has not been reached, a further iteration is performed in step 65. The updated model from step 61 is used in order to calculate, using the inverse kinematic solutions, the robot movement necessary to move the needle tip towards the intended target in the next incremental step, preferably taking into account the optimization for minimal needle deflections, or minimum tissue distortion. To this calculated new target point is also added the error correction from step 62, and the robot is then instructed to move to this combined next desired iteration position.

Once the new incremental movement has been performed, the process flow returns to step 57, where the new trajectory is determined from the needle image obtained, and the process repeats itself, until the final iteration has been performed and the intended target reached.

Figure 11:
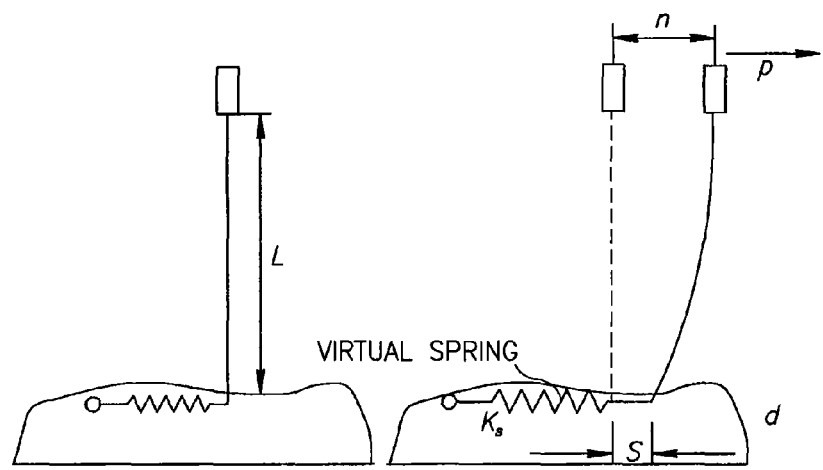
FIG. 11 illustrates a method of estimating the initial tissue stiffness coefficient by measuring the force and the deflection of the needle tip while just touching the top surface of the tissue.

Reference is now made to FIG. 11, which illustrates a method of estimating the initial tissue stiffness coefficient by measuring the force and the deflection of the needle tip while just penetrating the top surface of the tissue. The equivalent stiffness coefficient of the needle in this case is calculated from $k_n = 3EI/L^3$ and the stiffness coefficient of the virtual spring is proportional to the ratio of needle base to tip displacement $k_s/k_n = (n-s)/s$.

Prior to needle insertion the needle tip trajectory is examined to verify that the robot is capable of executing the movements required to achieve the required path and that the needle deflections are in the range of linear deflection approximation.

A single fluoroscopic image is taken in order to plan the needle tip trajectory just before the insertion. The needle tip, the obstacle and the target are detected on the image as described above, and through these three points a spline trajectory is constructed with the following constraints:
1. The trajectory is tangential to the needle at the tip.
2. The trajectory passes above or below the obstacle by a predetermined distance.
3. The curvature of the spline at the target point is zero.

Figure 12:
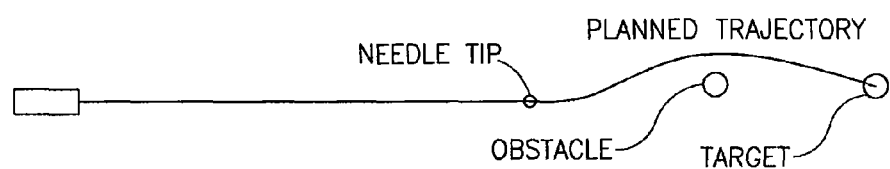
FIG. 12 shows a typical needle insertion trajectory plan.

A typical trajectory plan is shown in FIG. 12.

By relaxing the requirement that tip orientation be tangential to the path at each point, it is possible to greatly decrease both the needle base stroke and the lateral pressure exerted on the tissue.

Based on the required trajectory, inverse kinematics are calculated for each incremental needle movement.

After the trajectory has been verified for attainability and acceptable applied force, the software is commanded to start the execution. Using currently available C-arms, dynamic images can be acquired with sufficient quality to allow the insertion process to be completed in several seconds.

The operator behind a lead shield can observe the needle insertion scene on the USB camera as shown in FIG. 10. In case of emergency, the user can stop the whole procedure and retract the needle.

Qualitative tissue property measurements using the above described system, showed a 220 N/m stiffness for the first tissue spring approximation. During the insertion the estimated stiffness coefficients were between 200 N/m and 300 N/m, which is a similar magnitude to the stiffness coefficients found in the article by M. O'Leary, et al, entitled "Robotic Needle Insertion: Effects of Friction and Needle Geometry", published in IEEE International Conference on Robotics and Automation, 2003, pp. 1774-1780.

Figure 13:
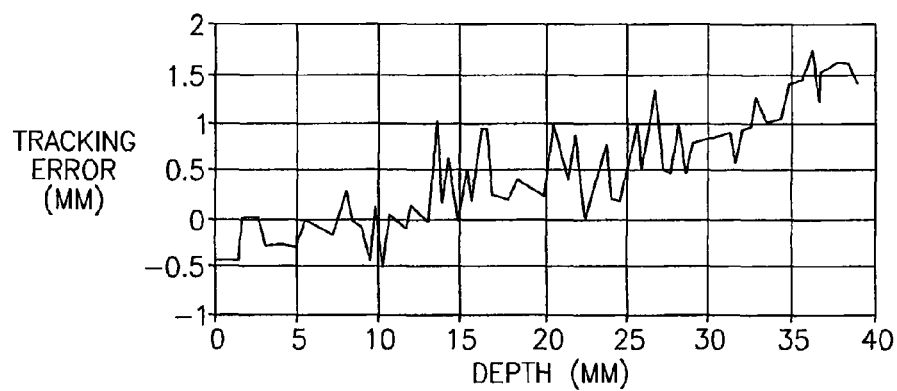
FIG. 13 is a graph showing the results of a flexible needle insertion along the preplanned trajectory performed in open loop.
Figure 14:
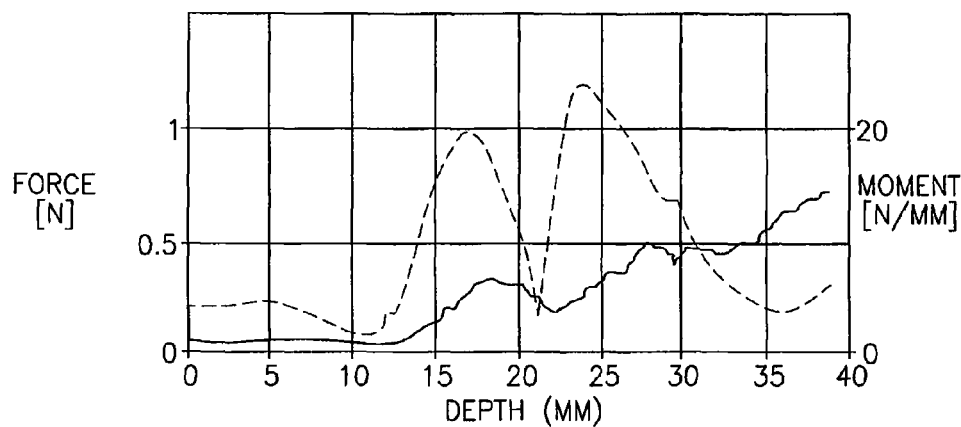
FIG. 14 shows the force and torque as measured at the base of the needle by the force sensor during the insertion procedure shown in FIG. 13.

Reference is now made to FIG. 13, which is a graph showing the results of a flexible needle insertion along the preplanned trajectory performed without control feedback. This means that the needle tip is not detected, the error from the preplanned trajectory is not calculated and there are no on-line corrections to the robot movements. Everything is done as if the real tissue behaves as a perfect match to the model used in determining the robot movements needed for the needle tip to follow the preplanned trajectory. Since, however, the real tissue behaves differently, and there may be other factors like needle material, or patient movements, the error accumulates in time. The ordinate shows the tracking error of the tip from the pre-planned trajectory as a function of needle insertion. The force and torque as measured at the base of the needle by the force sensor are shown in FIG. 14. The dashed line in FIG. 14 is the torque, and the full line is the force.

Figure 15:
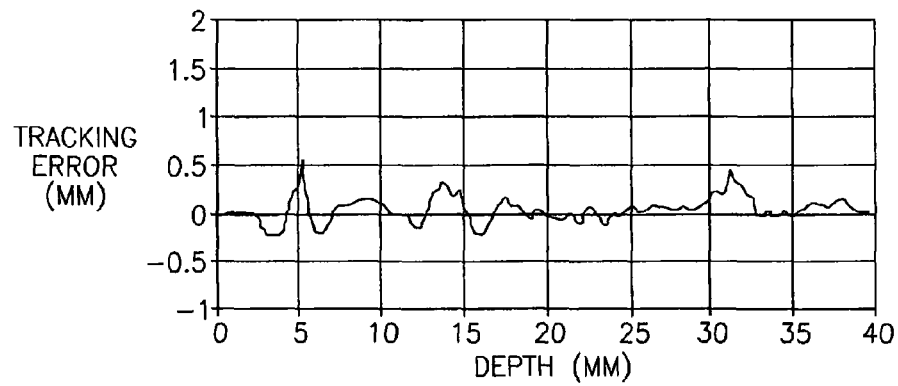
FIG. 15 is a graph showing the results of needle insertion along the same trajectory as in FIG. 13, but controlled by a PID controller using the control algorithm of the present invention.

Reference is now made to FIG. 15, which is a graph showing the needle insertion along the same trajectory, but this time controlled by a PID controller using the control algorithm of the present invention, as described above, with Kp=0.5 and Ki=0.001. The ordinate shows the tracking error of the tip from the pre-planned trajectory. The force and torque as measured by the force sensor at the base of the needle are shown in FIG. 16.

Figure 16:
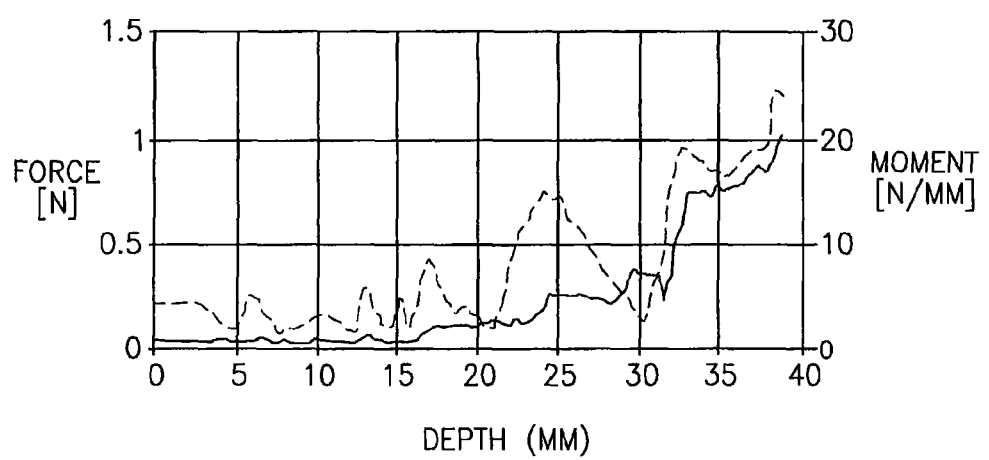
FIG. 16 shows the force and torque as measured at the base of the needle by the force sensor during the insertion procedure shown in FIG. 15.

As is observed by comparison of the situations with (FIG. 15) and without (FIG. 13) a control system for executing the insertion procedure, the tracking error reaches 1.5 mm if no control is applied, but with PID control the tracking error remains below 0.5 mm (FIG. 16). From comparison of FIGS. 14 and 16, it is seen that the force applied on the needle base is 25% greater during the controlled insertion while the moment is of the same magnitude. It can thus be seen that the controlled flexible needle manipulation procedure, according to the various embodiments of the present invention, does not requires significant additional forces, and that the control successfully maintains the tracking error within significantly closer boundaries than without use of the control system.

It is to be understood that the control scheme used in the above-described preferred embodiment of the present invention is only one alternative method, and that the invention is not meant to be limited to use of that scheme, but is meant to include applications using other controllers and other control schemes. Furthermore, although the invention has been described using control in only 2-dimensions, it is to be understood that this is only for purposes of explanation of the system and its method of operation, and that the method and apparatus are equally useable with 3-dimensional controlled motion.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

The invention claimed is:

1. A system for the insertion of a needle having a tip into a tissue, according to a predetermined trajectory, comprising:
 a robot for maneuvering said needle into said tissue;
 an imaging system for ascertaining the trajectory of said needle in real time; and
 a control system controlling said robot motion according to differences between said ascertained trajectory and said predetermined trajectory,
 wherein said controller utilizes a model of said needle as a flexible beam having a plurality of virtual springs each having a coefficient of stiffness connected laterally thereto to simulate lateral forces exerted by said tissue on said needle, and whose trajectory through said tissue is determined by the influence of said plurality of virtual springs on said needle, and wherein said system determines the needle trajectory taking into account the change in the stiffness coefficients of at least some of said virtual springs as a result of the trajectory of said needle and said control system utilizes an inverse kinematics solution applied to said virtual springs model to calculate the required motion to be imparted to said needle to follow said planned trajectory.

2. A system according to claim 1 wherein said system determines the needle trajectory taking into account the effect of motion of said tissue as a result of insertion of said needle.

3. A system according to claim 1, wherein said robot motion comprises at least some of inward, lateral and angular motion.

4. A system according to claim 3, wherein said robot motion comprises up to 6 degrees of freedom.

5. A system according to claim 1 wherein said imaging system is any one of an X-ray fluoroscopic system, a CT system, an MRI system, an ultrasonic system, a system using electromagnetic navigation, and a system using optical navigation.

6. A system according to claim 1 wherein said imaging system is aligned to provide images of a plane generally including the directions of said lateral and inward motion.

7. A system according to claim 1 wherein said control system determines the deviation of the real time position of said tip determined by image processing of an image obtained from said imaging system, from the planned position of said tip according to said predetermined trajectory, and calculates the motion to be applied to said robot to reduce said deviation by use of said virtual springs model.

8. A system according to claim 1, wherein said predetermined trajectory is divided into increments, and the control system performs the insertion according to these increments, and in accordance with the real time results obtained at least from the imaging system at each incremental insertion point.

9. A system according to claim 1, further comprising a registration system such that the co-ordinate system of said robot, to which said needle is attached, can be related to the co-ordinate system of the imaging system.

10. A system according to claim 1, wherein said predetermined trajectory of said needle comprises a target for said tip of said needle.

11. A system according to claim 10 wherein said predetermined trajectory is adapted to avoid at least one region where access is forbidden to said needle.

12. A system according to claim 1 wherein said control system uses the shape of the needle as detected from the images, to determine in real time changes in the stiffness properties of the tissue which the needle is traversing.

13. A system according to claim 12 and wherein said control system uses these changed tissue properties to adjust the needle path in real time in accordance with the tissue being negotiated.

14. A system according to claim 12, further comprising a force sensor to determine the forces exerted on said needle at its base, and wherein said control system also uses said forces to determine in real time changes in the stiffness properties of the tissue which the needle is traversing.

15. A system for the insertion of a needle having a tip into a tissue, according to a predetermined trajectory, comprising:
a robot for maneuvering said needle into said tissue;
a plurality of position sensors disposed along said needle for ascertaining the trajectory of said needle in real time;
a registration system to relate a co-ordinate system of said robot to which said needle is attached to the ascertained position of the needle; and
a control system controlling said robot motion according to differences between said ascertained trajectory and said predetermined trajectory,
wherein said controller utilizes a model of said needle as a flexible beam having a plurality of virtual springs each having a coefficient of stiffness connected laterally thereto to simulate lateral forces exerted by said tissue on said needle, and whose trajectory through said tissue is determined by the influence of said plurality of virtual springs on said needle, and wherein said system determines the needle trajectory taking into account the change in the stiffness coefficients of at least some of said virtual springs as a result of the trajectory of said needle,
such that the position of said needle can be determined without the use of X-ray imaging and said control system utilizes an inverse kinematics solution applied to said virtual springs model to calculate the required motion to be imparted to said needle to follow said planned trajectory.

16. A system according to claim 15, wherein said at least one position sensor is an electromagnetic position sensor.

17. A system for controlling the insertion of a needle into a deformable tissue, according to a predetermined trajectory, comprising:
a robot for maneuvering said needle into said tissue;
an imaging system for ascertaining the trajectory of said needle in real time; and
a control system adapted to control said robot motion according to differences between said ascertained trajectory and said predetermined trajectory;
wherein said control system is adapted to:
(i) use the trajectory of the imaged needle to determine changes in the elastic properties of the tissue along the path through which the needle is passing;
ii) utilize these tissue properties to adjust, according to the tissue being negotiated, an elastic model of the tissue along the path of the needle, said elastic model being based on a plurality of virtual springs, each having a coefficient of stiffness, said springs acting on the needle modeled as a flexible beam;
(iii) obtain an inverse kinematic solution for the motion of said needle along its path through said tissue; and
(iv) instructs said robot to maneuver said needle into said tissue according to said solutions,
and wherein said system determines the needle trajectory in accordance with changes in said elastic model of the tissue, as the needle passes through said tissue.

18. A system according to claim 17, and further comprising a force sensor to determine the forces exerted on said needle at its base, and wherein said control system is adapted to performs the additional step of also using said forces to determine changes in the elastic properties of the tissue which the needle is traversing.

19. A system according to claim 17, and wherein said predetermined trajectory is divided into increments, and said control system performs said insertion incrementally according to the real time results obtained from said imaging system.

20. A method of controlling the insertion of a needle into a tissue, comprising the steps of:
determining a preplanned trajectory to be followed by said needle;
mounting the base of said needle on a robot for maneuvering said needle into said tissue;
generating images of said tissue to show the trajectory of said needle in real time;
controlling the motion of said robot according to differences between said real-time trajectory and said preplanned trajectory; and
utilizing a model of said needle as a flexible beam having a plurality of virtual springs each having a coefficient of stiffness connected laterally thereto to simulate lateral forces exerted by said tissue on said needle, and calculating said trajectory through said tissue on the basis of the influence of changes in the coefficient of stiffness of at least some of said plurality of virtual springs on said needle and said control system utilizes an inverse kinematics solution applied to said virtual springs model to calculate the required motion to be imparted to said needle to follow said planned trajectory.

* * * * *